United States Patent
Dunkley et al.

(10) Patent No.: US 9,375,500 B2
(45) Date of Patent: *Jun. 28, 2016

(54) STERILISATION AND DECONTAMINATION DEVICE

(71) Applicant: DOW GLOBAL TECHNOLOGIES LLC, Midland, MI (US)

(72) Inventors: Peter Dunkley, Birlingham (GB); Joshua Denne, Birlingham (GB)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,994

(22) Filed: Mar. 10, 2015

(65) Prior Publication Data

US 2015/0182649 A1 Jul. 2, 2015

Related U.S. Application Data

(62) Division of application No. 13/394,607, filed as application No. PCT/GB2010/001694 on Sep. 7, 2010, now Pat. No. 9,011,787.

(30) Foreign Application Priority Data

Sep. 7, 2009 (GB) .................... 0915487.3

(51) Int. Cl.
| | |
|---|---|
| *A61L 2/20* | (2006.01) |
| *A61L 9/015* | (2006.01) |
| *A61L 9/12* | (2006.01) |
| *C01B 13/10* | (2006.01) |
| *F24F 3/16* | (2006.01) |
| *F24F 6/14* | (2006.01) |

(52) U.S. Cl.
CPC ................ *A61L 2/202* (2013.01); *A61L 9/015* (2013.01); *A61L 9/12* (2013.01); *C01B 13/10* (2013.01); *A61L 2202/25* (2013.01); *C01B 2201/64* (2013.01); *C01B 2201/72* (2013.01); *C01B 2201/90* (2013.01); *F24F 3/16* (2013.01); *F24F6/14* (2013.01); *F24F 2003/1685* (2013.01); *F24F 2006/146* (2013.01); *F24F 2221/125* (2013.01)

(58) Field of Classification Search
CPC ........... A61L 2/202; A61L 9/015; A61L 9/12; A61L 2202/25; C01B 13/10; C01B 2201/64; C01B 2201/72; C01B 2201/90; C01B 13/11; C01B 13/115; C01B 2201/74; F24F 3/16; F24F 6/14; F24F 2003/1685; F24F 2006/146; F24F 2221/125; B01J 19/088; B01J 19/087
See application file for complete search history.

(56) References Cited

U.S. PATENT DOCUMENTS

| | | |
|---|---|---|
| 5,641,461 A | 6/1997 | Ferone |
| 2008/0206096 A1 | 8/2008 | Deka |
| 2008/0310992 A1 | 12/2008 | Heselton et al. |

FOREIGN PATENT DOCUMENTS

| | | |
|---|---|---|
| EP | 1293216 | 3/2003 |
| EP | 1500404 A1 | 1/2005 |
| JP | 2001-286542 | 10/2001 |
| JP | 2004-166742 | 6/2004 |
| JP | 2005-083652 | 3/2005 |
| WO | 2008014615 | 2/2008 |

OTHER PUBLICATIONS

International Search Report Issued Jun. 12, 2010 in International Patent Application Serial No. PCT/GB2010/001694.

*Primary Examiner* — Xiuyu Tai
(74) *Attorney, Agent, or Firm* — Tifani M. Edwards

(57) ABSTRACT

A sterilization, sanitization and/or decontamination device 1 comprising at least a humidifier unit, an ozone generator unit 60, at least one discharge outlet 16 and a controller for controlling the humidifier and ozone generator units, the at least one discharge outlet 16 comprising at least two at least partially converging plates 72, 74 between which substances are discharged.

4 Claims, 8 Drawing Sheets

STERILISATION AND DECONTAMINATION DEVICE

CROSS REFERENCE TO RELATED APPLICATIONS

This application claims priority to, and is a divisional of, U.S. application Ser. No. 13/394,607 filed May 23, 2012, titled "A Sterilisation and Decontamination Device," which claimed priority to PCT Application No. PCT/GB2010/001694, filed Sep. 7, 2010, and which claimed priority to UK Application No. 0915487.3, filed Sep. 7, 2009, all of which are incorporated by reference herein as if reproduced in full below.

BACKGROUND

This invention relates to an improved sterilisation, sanitisation and/or decontamination device.

It is a requirement to sterilise and sanitise enclosed spaces, such as kitchen areas and hospital rooms quickly and effectively, to destroy potentially harmful micro-organisms, such as bacteria and viruses, contaminating the air and surfaces there within, in an acceptable timescale.

The biocidal activity of ozone is widely known and appreciated, and it is also known that the provision of ozone in a humid atmosphere increases the biocidal effectiveness.

However, problems associated with the use of ozone as a biocide have been the relatively lengthy post-treatment process to ensure that the environment is safe for returning occupants, the use of potentially environmentally damaging chemicals during the process, the general ineffectiveness of the process package in sanitising the environment, and the overall lack of simplicity in quickly setting up and using the apparatus.

The Applicant's previous application EP 1500404 (Steritrox Limited) and unpublished pending GB Application No.s 0904262.3, 0904264.9, 0904266.4, 0904269.8 and 0904272.2 relate to their methods for decontamination of an environment using the beneficial effect of ozone in a humid atmosphere. Whilst these processes are efficient at providing a sterile environment, it is desirable to provide an apparatus that allows for sufficient humidity levels to be reached within the area to be treated without condensation or puddling of the water vapour. Any condensation of water on surfaces acts as a barrier to the reaction and may also result in a damp room when the treatment has been completed.

The present invention seeks to provide a solution to this problem, in particular to provide a sterilisation, sanitisation and/or decontamination device that provides satisfactory humidity levels with minimal or no condensation of water vapour.

SUMMARY

According to the present invention, there is provided a sterilisation, decontamination and/or sanitation device, the device comprising at least a humidifier unit, an ozone generator unit, at least one discharge outlet and a controller for controlling the humidifier and ozone generator units, the at least one discharge outlet comprising at least two at least partially converging plates between which substances are discharged.

Preferably, ozone generated by the ozone generator unit is discharged through the discharge outlet comprising at least two at least partially converging plates. More preferably, the ozone generator is provided within, or attached to, a delivery conduit that leads to the discharge outlet. Preferably, a fan is provided at the base of the conduit for moving air and ozone through the conduit and out of the discharge outlet.

Preferably, the lower plate has an angle of inclination that is between 1-5 degrees greater than the upper plate. In particular, it has been found that a lower plate having an angle of inclination of 17° above the horizontal and an upper plate having an angle of inclination of 15° above the horizontal provides the required acceleration of air flow through the discharge outlet.

It is preferable for the plates to be in the form of discs. Preferably, the plates are at least 200 mm in diameter, more preferably between 250-350 mm in diameter, especially being 300 mm in diameter.

The distance between the plates is preferably as short as possible whilst providing for satisfactory discharge and mixing of the air and water droplets. Preferably, the distance between the plates is between 50-200 mm, preferably 100-175 mm, especially 150 mm.

Preferably, the humidifier comprises a water reservoir and at least one discharge nozzle for releasing water droplets as a fine spray. Preferably, the at least one discharge nozzle is attached to the upper plate of the discharge outlet, remote from the lower plate. In this manner, the water droplets are supported by the airstream discharged from the discharge outlet.

Preferably, the humidifier, water reservoir, ozone generator, controller and conduit are provided within a housing with the discharge outlet extending from the intended upper surface of the housing. It is to be appreciated that the housing may include additional components for optimization of the operation of the device, such as a hydrocarbon discharge unit and/or a UV catalyst, appropriate sensors, a fan, an oxygen supply and/or a water reservoir.

The positioning of the converging plates of the discharge outlet relative to the housing has also found to be important. A spacer element providing a minimum distance of 50 mm between the top of the housing and the lower plate is preferred, more preferably being at least 150 mm, especially 160 mm. Additionally or alternatively, the peripheral edges of the plate should extend beyond the periphery of the spacer element, preferably by at least 1 mm, preferably 5 mm.

A cover plate may be provided over the discharge nozzles attached to the upper plate. Preferably, the cover plate is contoured such as to reduce laminar air flow and to direct any water towards a drainage collection point provided within the cover.

A mesh or gauze is preferably provided across the opening between the upper and lower plates.

A second aspect of the present invention provides a delivery and discharge outlet assembly for an air decontamination device, the assembly comprising an ozone generator provided within, or attached to, a delivery conduit, the delivery conduit having at one end thereof at least one discharge outlet comprising at least two at least partially converging plates between which substances are discharged.

Preferably, a fan is provided at the end of the conduit remote from the discharge outlet. Preferably, at least one water discharge nozzle is attached to the upper plate of the discharge outlet, remote from the lower plate. A cover plate may be provided over the water discharge nozzle and/or a mesh may be provided over the opening between the upper and lower converging plates.

BRIEF DESCRIPTION OF THE DRAWINGS

The invention will now be more specifically described, by way of example only, with reference to the accompanying drawings, in which.

DETAILED DESCRIPTION

Referring now to the accompanying drawings, there is shown an example of a sterilisation and decontamination device 1 according to one embodiment of the present invention. The apparatus comprises a portable enclosure 1 having a main body 10 and a detachable control panel 12. In the embodiment shown, the control panel is in the preferred form of a detachable lectern but it is to be appreciated that the invention is not limited thereto and that the control panel may be provided elsewhere on the enclosure or remote thereto.

Figure 8:
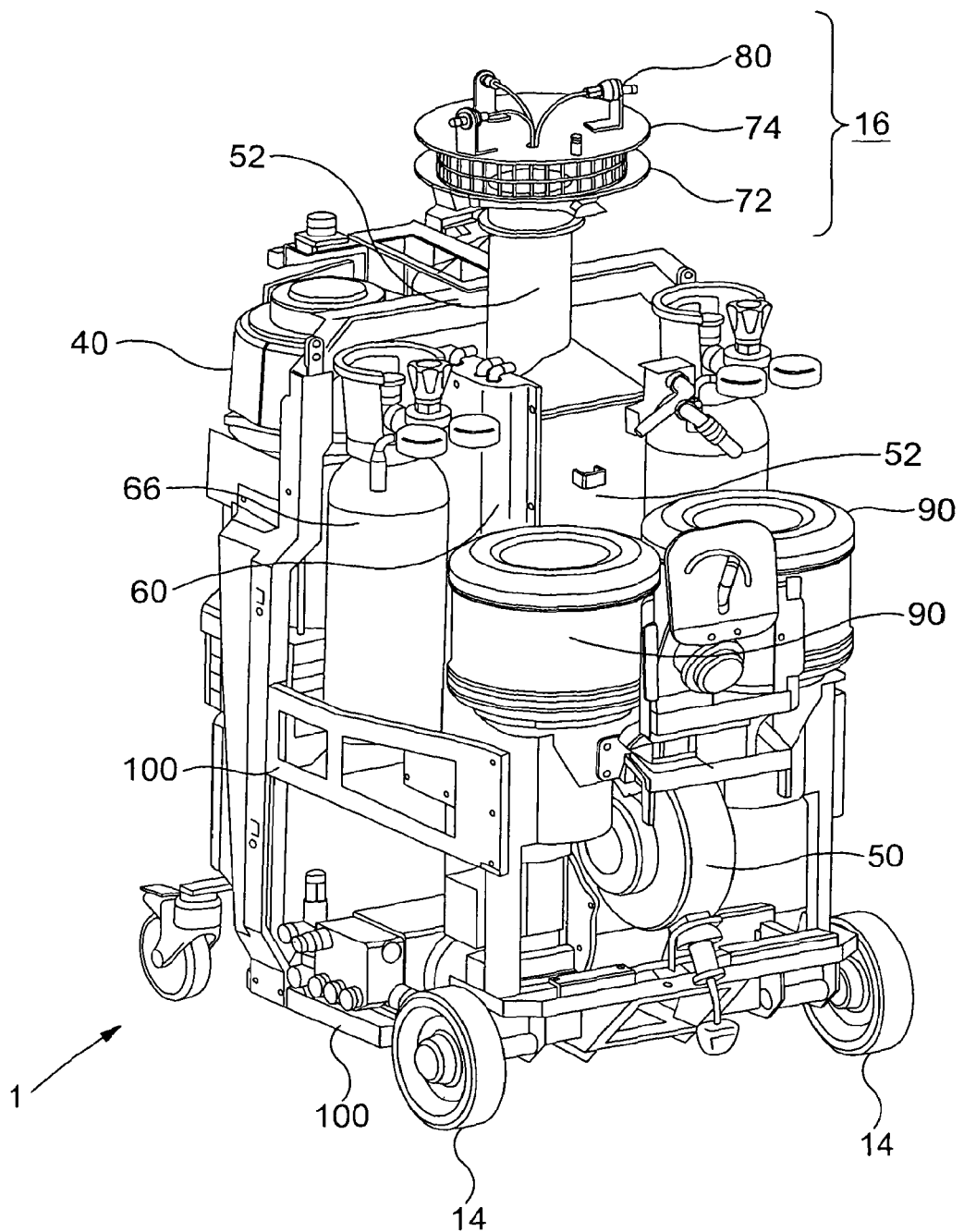
FIG. 8 illustrates the internal components of the sterilisation and decontamination device shown in FIG. 1.

The main body 10 has wheels 14 and handles 15 and houses the components of the device (see, in particular, FIG. 8) that are required for carrying out the decontamination process, in particular a humidifier unit and an ozone generator unit. The main body may also include a catalyst 40 and/or a hydrocarbon generator unit for supplying a hydrocarbon containing a carbon-carbon double bond and/or for aiding removal of by-products. A discharge outlet assembly 16 extends from the top of the main body to discharge the required substances into the atmosphere and a microprocessor is provided within the unit for controlling discharge from the outlet assembly.

The humidifier unit generally includes a humidifier, a humidistat sensor, a temperature sensor and a water reservoir 90. The humidifier releases water droplets from the discharge outlet assembly 16. The water droplets have a diameter of less than 5 microns, preferably 2-3 microns, to enhance the rate of evaporation into the atmosphere. The ozone generator unit includes an ozone generator 60, an ozone detector sensor, and an oxygen supply 62 for supplying oxygen to the ozone generator. All these components are housed within or on the housing forming the main body 10.

Figure 1:
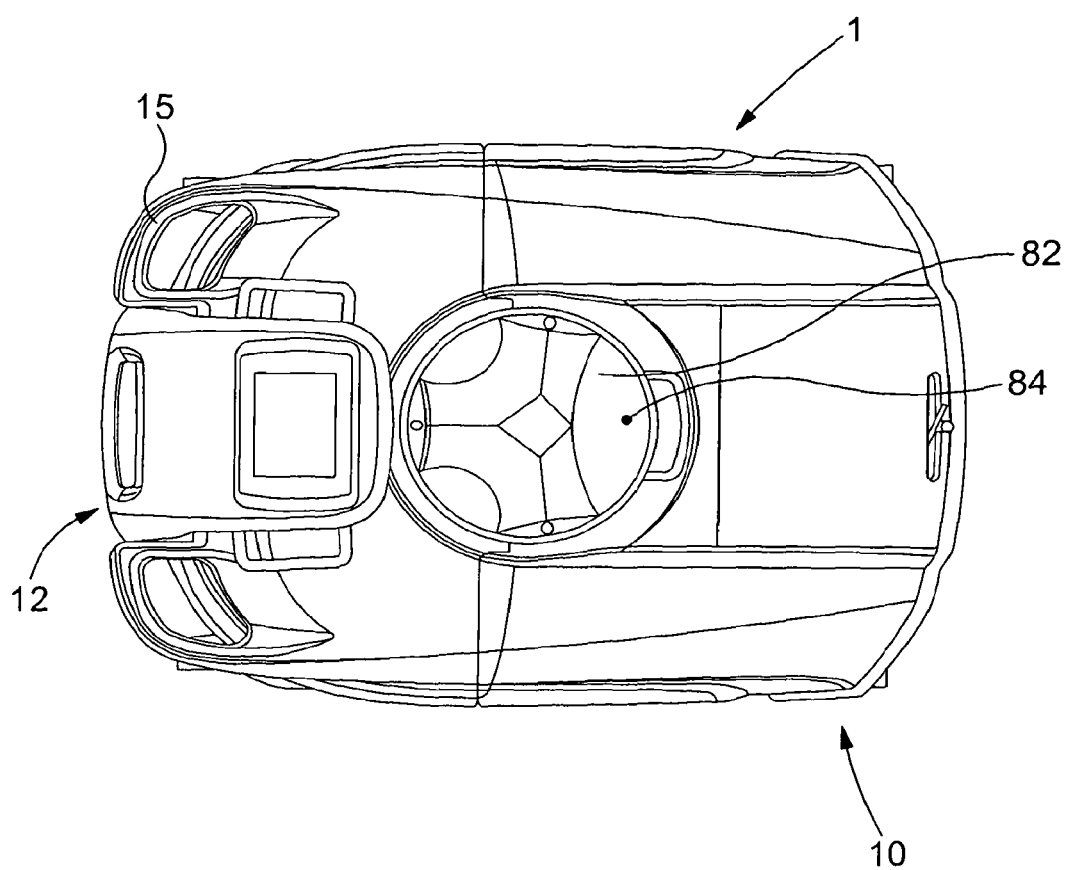
FIG. 1 is plan top elevation external view of a sterilisation and decontamination device according to one embodiment of the present invention.
Figure 2:
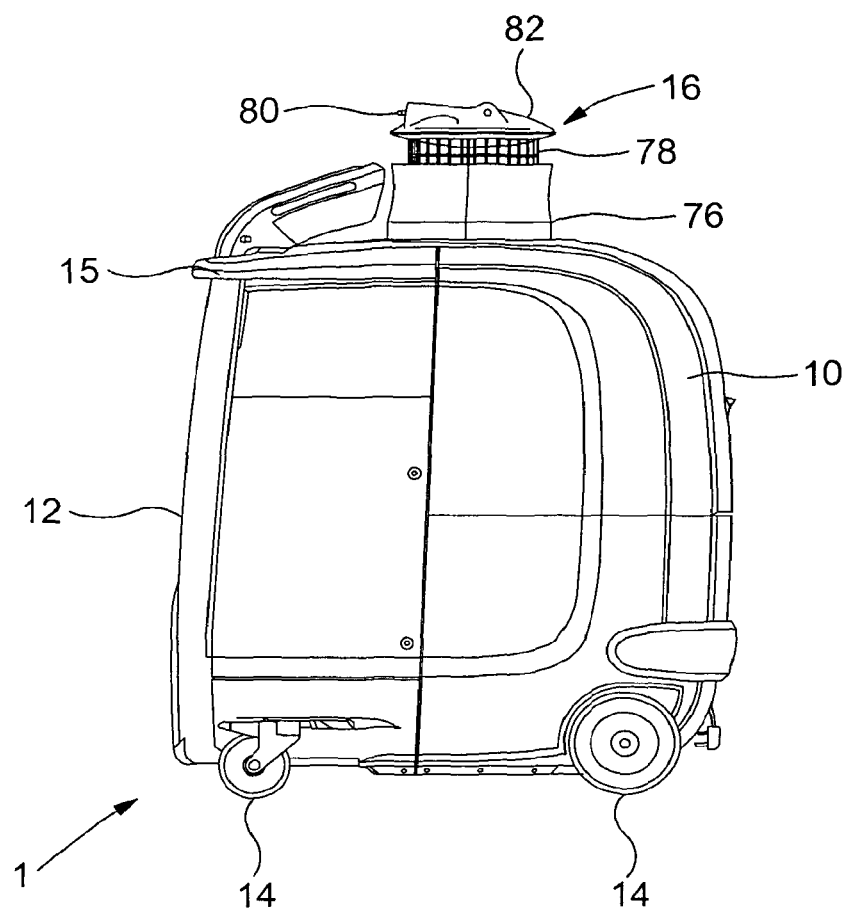
FIG. 2 is a side elevation external view of the device shown in FIG. 1.
Figure 3:
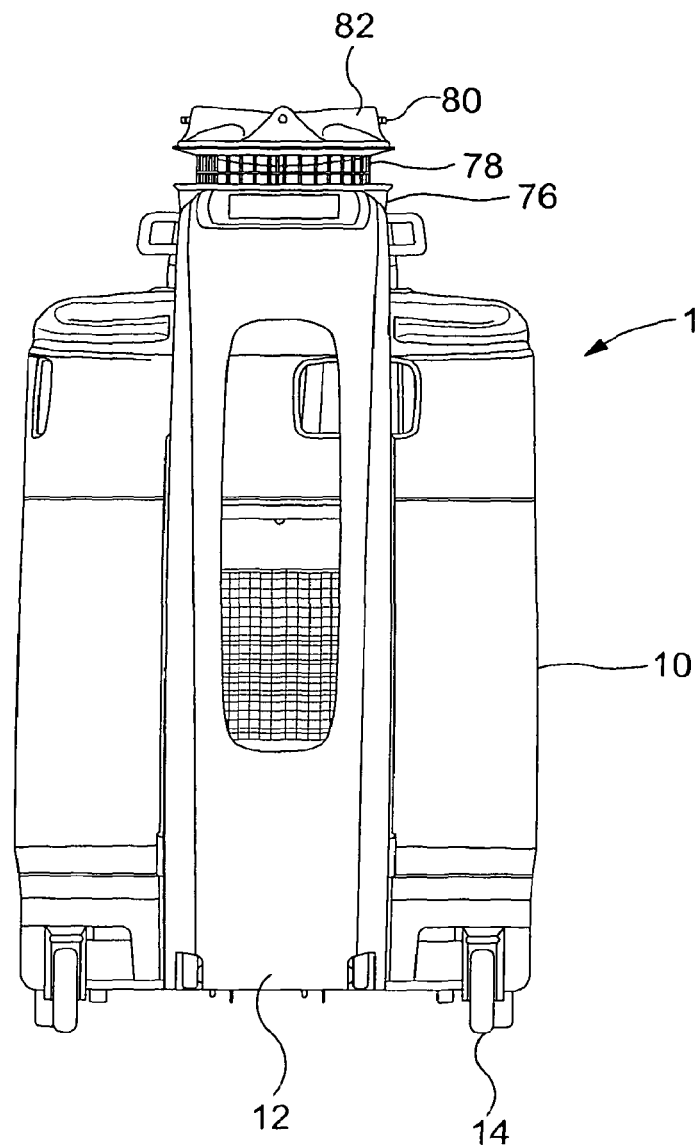
FIG. 3 is a rear elevation external view of the device shown in FIG. 1.
Figure 4:
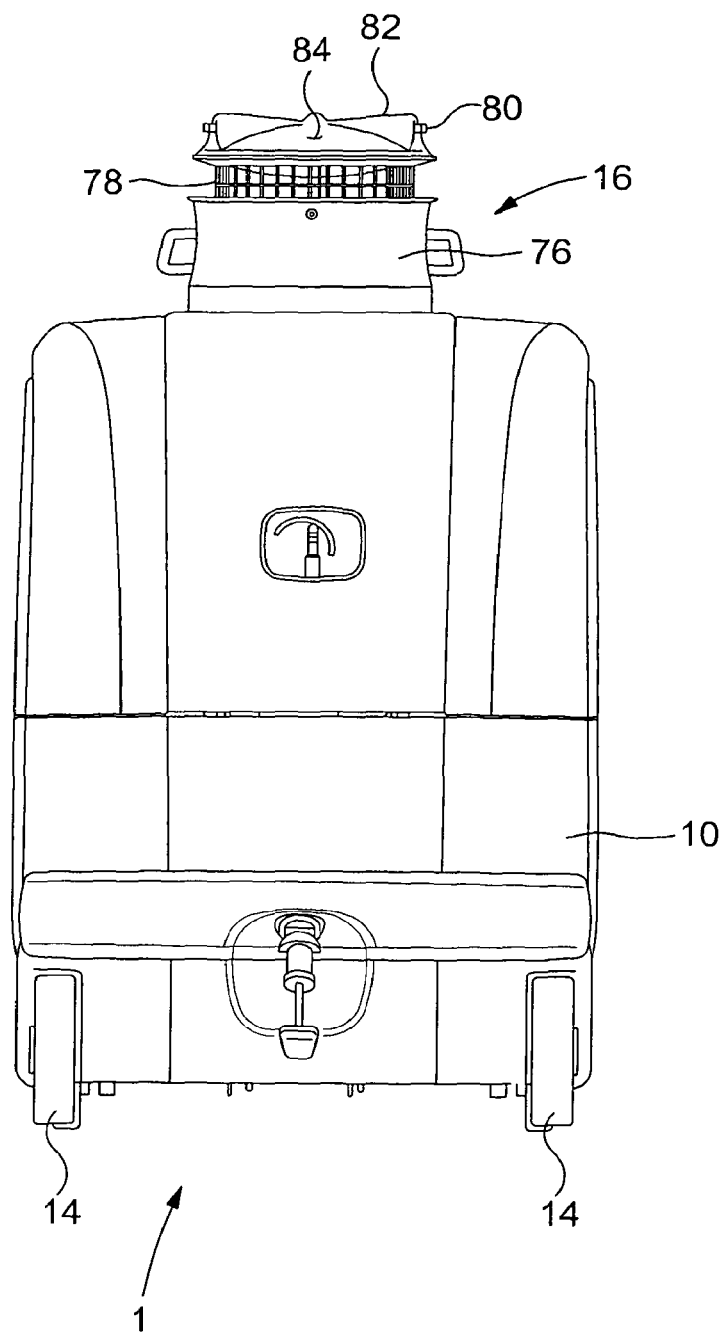
FIG. 4 is a front elevation external view of the device shown in FIG. 1.
Figure 5:
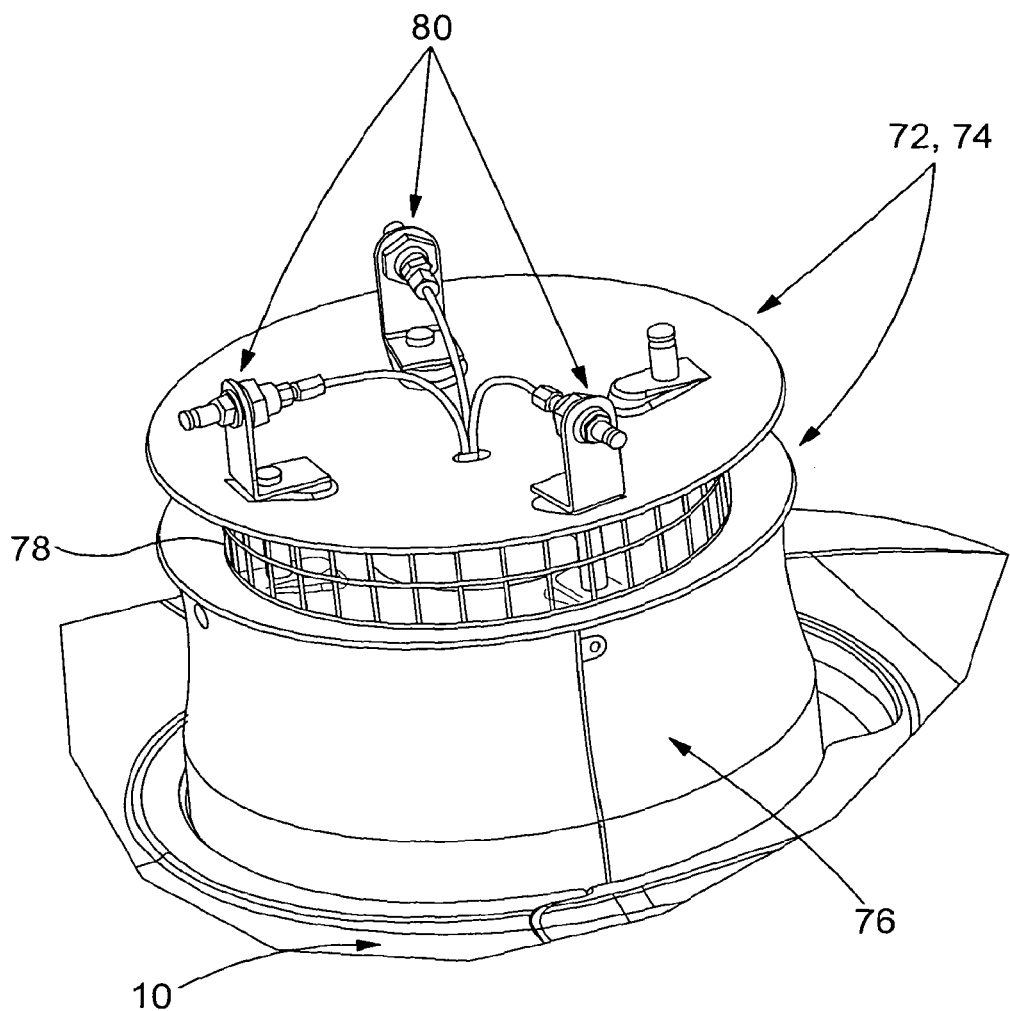
FIG. 5 is perspective view of the discharge outlet assembly of the device shown in FIG. 1, shown without a cover plate.
Figure 6:
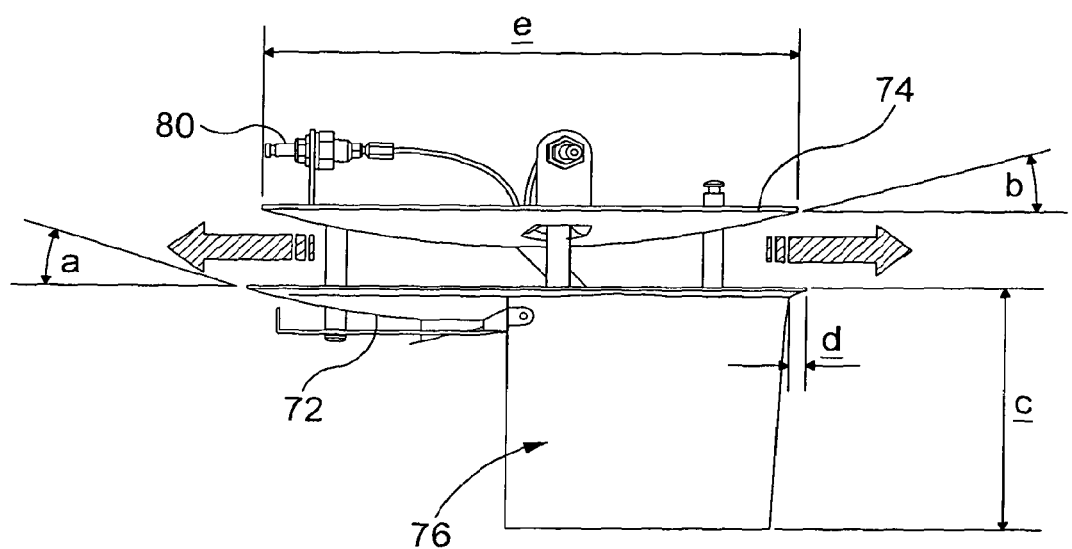
FIG. 6 is a schematic diagram of the arrangement of the components in the discharge outlet assembly shown in FIG. 5.
Figure 7:
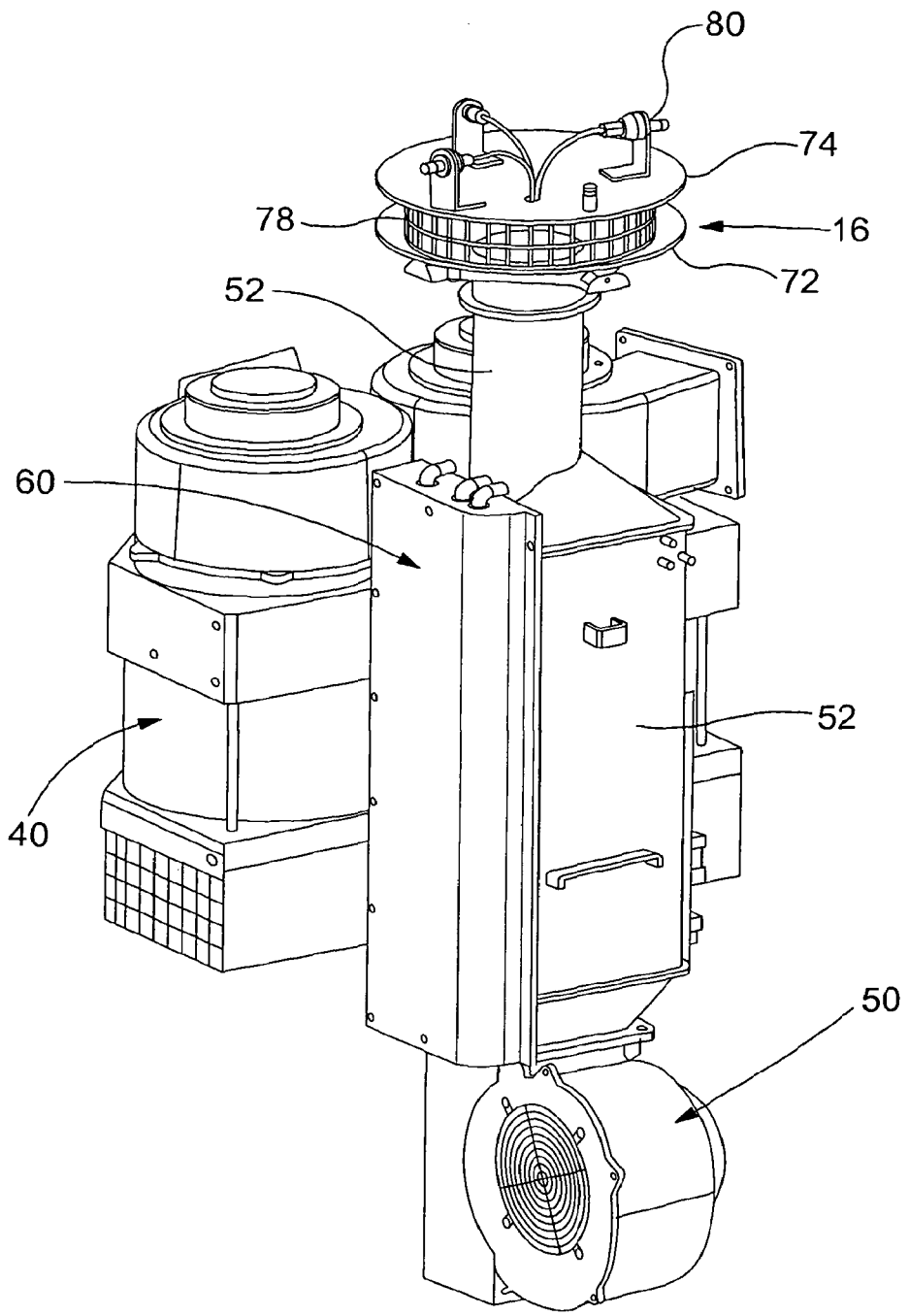
FIG. 7 is a schematic diagram of the components of the delivery unit connected to the discharge outlet assembly shown in FIG. 5.

In order for the device to achieve the required biocidal activity, high levels of humidity have to be achieved in a short time period in the area to be treated. This can lead to condensation wherein water is deposited on surfaces within the room being treated and a damp feeling is left in the room when it is re-occupied. The device of the present invention reduces the level of condensation by the provision of a specially designed delivery tube and discharge outlet assembly as shown in the accompanying drawings, in particular FIGS. 5 to 7. A common fan 50 is provided at the base of a delivery tube 52 which includes the ozone generator 60. The upper end of the tube leads to the discharge outlet 16 which comprises a 360 degree high volume air outlet. The discharge outlet assembly comprises a pair of converging plates 72, 74, preferably in the form of discs, between which the air containing the ozone, is discharged. Water discharge nozzles 80 are attached to the upper surface of the top plate 74 to introduce sterile, demineralised water to the atmosphere. One or more water reservoirs 90 deliver water to a compressor (not shown) which in turn delivers high pressure water (at least 50 Bar) to the discharge nozzles. A cover or cap 82 is fitted over the water discharge nozzles, the cover being contoured such as to direct any water to a drainage collection point 84.

The first lower plate 72 is spaced apart from the top of the enclosure 10 by means of a spacer element 76. The spacer element preferably provides a distance of at least 50 mm, more preferably at least 150 mm, between the top of the enclosure 10 and the plate 72 (distance "c" in FIG. 6). The plates in the illustrated embodiment are 300 mm in diameter (distance "e") but need not be so. The outer periphery of the plate 72 extends approximately 5 mm beyond the periphery of the spacer element (distance "d" in FIG. 6). A mesh or gauze 78 is provided between the converging plates to prevent the ingress of any foreign objects.

The concave plates have different angles of inclination to provide a converging arrangement. The difference in these angles may vary but it has been found that the lower disc having an angle of inclination that is between 1-5 degrees greater than the upper disc provides sufficient acceleration of the air flow that is discharged from the delivery tube through the outlet to create a cushion of air that supports the atomised water droplets discharged through the nozzles 80 whilst they are absorbed into the atmosphere before they can drop out onto surrounding surfaces and dampen then. In the illustrated embodiment, lower plate 72 has an angle a of inclination of 17° above the horizontal and upper plate 74 has an angle b of inclination of 15° above the horizontal.

The design of the cover plate, top disc and spacer element are such as to minimise lamination of the expelled air onto the cover plate and surrounding body work respectively. A reduction in laminar flow of the expelled air stream prevents or minimises hugging of the bodywork of the machine by the air and water droplets which cause condensation to run off the machine and puddle on the floor. The accelerated air flow provided by the converging plates also results on the atomised water droplets lying on a bed of fast flowing air which assists in supporting the droplets whilst they are absorbed into the atmosphere.

The arrangement of the delivery tube and discharge outlet assembly is such that a single fan can be used not only to create the required airflow but also to provide a cooling airflow for the ozone generators and aid mixing of the ozone within the delivery tube. This has clear financial and weight benefits. The particular arrangement of the discharge outlet assembly has been found to allow superior mixing of the air in a room to be decontaminated thereby increasing the efficiency of the decontamination process.

If the device is to include a hydrocarbon discharge unit this too is housed within the main body and includes a hydrocarbon supply in the form of a tank or container containing the hydrocarbon having a carbon-carbon double bond, such as a secondary olefin, cis or trans, including cyclic olefins together with means to discharge the hydrocarbon through the discharge outlet.

Access to the interior of the main body 10 is provided by a removable, preferably lockable, side panel or lid. The main body 10 also includes part of a control unit in the form of a microprocessor which controls the apparatus 1 and may be preset with at least one sterilisation and decontamination routine. The control unit includes a controller and a user interface which is located on the detachable lectern 12 by which a user can wirelessly input commands to the main body to remotely control operation of the device.

The apparatus 1 may include an on-board battery and/or may be connectable to a mains power supply. Preferably, the main body 10 may be connected to a mains supply and the lectern 12 is battery-operated, being charged by power from the main body when the lectern is docked therein.

The apparatus 1 will also typically include other safety features, such as safety sensors, and software routines to prevent start-up or initiate shut-down in the event of a system failure.

In use, the whole device 1 comprising the main body 10 connected to the lectern 12 is wheeled into an area which is to be sterilised and/or decontaminated. The unit is correctly positioned and then the lectern is detached from the main body by lifting and tilting the lectern onto its wheels. The lectern is then wheeled out of the room and positioned across a door or other opening that allows access to the area being decontaminated. This acts as a warning and bollard to prevent any person entering the area. Furthermore, the lectern enables operation of the components within the main body to be controlled remotely from outside of the room by means of the user interphase connected wirelessly to the microprocessor controlling the main body within the room. During operation of the device, the display unit on the top part of the lectern may display a visible warning to inform personnel that the decontamination process is being carried out and that the area should be left unoccupied. The lectern may also provide a visible or audio message when decontamination is complete, informing the user that the room may be re-occupied. Other appropriate data and information may be stored for access by the user.

During operation of the device, the area is sealed and the control unit located on the main body undertakes appropriate initial safety checks such as checking the relative humidity. If the safety check is not passed, the apparatus 1 does not operate and outputs a suitable indication using warning lights which may be on one or both of the main body and the lectern. During operation of the process, safety checks are made continuously, and in the event of a system failure, the system defaults to a safe mode.

The controller continues to monitor the conditions provided by the device and once a calculated relative humidity level is reached, the controller activates the ozone generator and ozone is generated. The generated ozone is then fed into the discharging humidified airstream that passes through the discharge outlet 16. The controller provides a suitable indication that the ozone generator is operating, and monitors the ambient ozone levels through the ozone detector sensor.

Both the ozone and water vapour concentrations to be detected can be altered by means of the user interface. However a typical setting is 25 ppm v/v of ozone and 13.6 torr. Once the preset ozone and water vapour levels have been detected within the allotted interval, the controller enters a timing phase, known as the "dwell time".

The dwell time can also be altered using the remote user interface, for example, to one hour, and will depend on the degree and type of decontamination/sanitisation to be provided. For instance, contamination by spores or moulds, such as *clostridium difficile*, generally require a longer dwell time than contamination by bacteria, such as *listeria* and methicillin resistant *staphylococcus aureus* (MRSA).

During the dwell time, the ozone concentration and relative humidity are continuously monitored. If the ozone level falls below a predetermined threshold, the ozone discharge unit is reactivated to replenish the ozone levels. If the humidity falls below the calculated value, the humidifier unit is reactivated to restore the water vapour level.

Again, during the reactivation period, should either the ozone concentration or the relative humidity fail to reach the above-mentioned predetermined minima within a set time interval, for example 10 minutes, the controller aborts the sterilisation and decontamination routine and outputs a suitable indication.

After the dwell time has elapsed, the controller shuts down the various supply units and, if a hydrocarbon is to be supplied, operates a hydrocarbon discharge unit to discharge the hydrocarbon into the ambient environment. The hydrocarbon preferentially reacts with the residual ozone to accelerate the breakdown of the ozone, thereby offering faster user re-entry to the treated area.

When an ozone detector sensor detects that the ozone concentration levels are less than a predetermined value, for example 0.2 ppm or less, the controller shuts off supply of the hydrocarbon and outputs an indication that the sterilisation and decontamination routine is complete. Again this is visible on the user display of the lectern and, optionally, the main body of the machine. The ozone level of 0.2 ppm, depending on the size of the area being sterilised and decontaminated, is usually achieved in less than 3 to 4 minutes.

If the ozone detector sensor fails to indicate that the predetermined safe level of ozone has been reached within a predetermined time interval following introduction of the hydrocarbon, for example within 10 minutes, the controller outputs an indication warning of potentially hazardous ozone levels in the room. The controller may be programmed to allow a time interval to elapse in excess of the standard half-life of ozone before announcing that the room may be re-occupied.

The above-described apparatus utilises a method of producing an artificially high level of non-condensing humidity, and generating in-situ a high concentration of ozone. The materials of the apparatus are resistant to the corrosive effects of ozone and high humidity, and the solvent effects of the hydrocarbon.

It is thus possible to provide a device for decontamination of an area which is fast and effective, discrete and portable. The method may provide better than 99.99% effective sterilisation and/or decontamination of an area without an impact on the environment from harmful by-products. Rapid re-use of a contaminated area can thus be realised. The above-described method has proven to be lethal to a wide variety of pathogens, including bacteria such as Methicillin Resistant *Staphylococcus Aureus* (MRSA). The particular arrangement of the converging plates of the discharge outlet assembly enables air that is discharged therefrom to be in the form of a platform onto which water droplets can be laid to humidify the air within a room. Without this converging arrangement, the air flow exiting the discharge outlet is insufficient to prevent some of the water droplets dropping out onto the floor and surrounding surfaces. Furthermore, the spacer element and cover plate reduce lamination of the expelled air which can again lead to condensation of the water vapour.

The device according to the present invention is able to facilitate both atmospheric and surface decontamination of a hospital room within just one hour. The device is such that is can be wheeled into a vacated room and be activated from outside the room by janitorial staff with minimal training using a simple touch screen control pad. The entire process requires minimal supervision while the intelligent control system constantly monitors room conditions and alerts staff when decontamination is complete or a problem is encountered.

The embodiments described above are given by way of examples only, and other modifications will be apparent to persons skilled in the art without departing from the scope of the invention as defined by the appended claims.

The invention claimed is:

1. An assembly comprising:
   an ozone generator provided within or attached to a delivery conduit, one end of the delivery conduit having a discharge outlet comprising at least two at least partially converging plates
   wherein the at least two partially converging plates comprise an upper plate and a lower plate; and
   a water discharge nozzle coupled to the upper plate of the discharge outlet, remote from the lower plate.

2. The assembly of claim 1 further comprising a fan disposed at the end of the delivery conduit remote from the discharge outlet.

3. The assembly of claim 1 wherein a cover plate is provided over the water discharge nozzle.

4. The assembly of claim 1 further comprising a mesh or gauze disposed over an opening between the upper and lower plates.

* * * * *